(12) United States Patent
Chiang et al.

(10) Patent No.: US 7,090,651 B2
(45) Date of Patent: Aug. 15, 2006

(54) COMPRESSION BRACE MATERIAL WITH SPACER FABRIC INNER LAYER

(75) Inventors: Jackson Chiang, Taipei (TW); Jonathon Chuang, Brisbane (AU)

(73) Assignee: La Pointique International Ltd., Tukwila, WA (US)

( * ) Notice: Subject to any disclaimer, the term of this patent is extended or adjusted under 35 U.S.C. 154(b) by 531 days.

(21) Appl. No.: 10/355,652

(22) Filed: Jan. 29, 2003

(65) Prior Publication Data

US 2003/0114782 A1 Jun. 19, 2003

Related U.S. Application Data

(63) Continuation-in-part of application No. 10/004,469, filed on Oct. 23, 2001, now Pat. No. 6,726,641, which is a continuation-in-part of application No. 09/846,332, filed on May 2, 2001, now Pat. No. 6,508,776.

(51) Int. Cl.
*A61F 5/00* (2006.01)
(52) U.S. Cl. .............................. 602/5; 602/26; 602/63; 602/65
(58) Field of Classification Search .................. 602/2, 602/5, 14, 20, 21, 42, 61–63; 428/67, 116
See application file for complete search history.

(56) References Cited

U.S. PATENT DOCUMENTS

| | | | |
|---|---|---|---|
| 2,570,182 A | 10/1951 | Daly et al. |
| 2,653,601 A | 9/1953 | Morrison |
| 2,976,539 A | 3/1961 | Brown, Jr. |
| 3,092,110 A | 6/1963 | Duensing |
| 3,328,505 A | 6/1967 | Spencer |
| 3,451,232 A | 6/1969 | Belzidsky |
| 3,600,717 A | 8/1971 | McKeehan |
| 3,892,239 A | 7/1975 | Masso Remiro |
| 3,990,440 A | 11/1976 | Gaylord, Jr. |
| 3,991,424 A | 11/1976 | Prahl |
| 4,043,058 A | 8/1977 | Hollister et al. |
| 4,084,586 A | 4/1978 | Hettick |
| 4,153,054 A | 5/1979 | Boone |
| 4,272,850 A | 6/1981 | Rule |
| 4,294,240 A | 10/1981 | Thill |
| 4,470,411 A | 9/1984 | Hoyt, Jr. |
| 4,516,572 A | 5/1985 | Schlein |
| 4,690,847 A | 9/1987 | Lassiter et al. |
| 4,832,010 A | 5/1989 | Lerman |
| 5,020,164 A | 6/1991 | Edwards |
| 5,656,352 A | 8/1997 | Middleton |
| 5,735,807 A | 4/1998 | Cropper |

(Continued)

FOREIGN PATENT DOCUMENTS

DE 36 13 488 A1 10/1987

(Continued)

*Primary Examiner*—Michael A. Brown
(74) *Attorney, Agent, or Firm*—Christensen O'Connor Johnson Kindness PLLC

(57) ABSTRACT

The present invention provides a composite material for use in making orthopedic elastic braces for supporting a body part by compression. One embodiment of the invention is a compression brace material (400) having an elastic outer layer (410), a first fabric layer (420), a spacer fabric layer (425), and a second fabric layer (430). The spacer fabric layer permits and promotes airflow laterally through the brace material. The outer layer may have a plurality of slits (550) therethrough to permit and promote airflow transversely through the composite material. The plurality of slits may be arcuate to further improve transverse airflow through the composite brace material.

18 Claims, 9 Drawing Sheets

U.S. PATENT DOCUMENTS

| | | |
|---|---|---|
| 5,901,379 A | 5/1999 | Hirata |
| 5,924,134 A | 7/1999 | Taylor et al. |
| 6,093,468 A | 7/2000 | Toms et al. |
| 6,110,135 A | 8/2000 | Madow et al. |
| 6,129,695 A | 10/2000 | Peters et al. |
| 6,190,344 B1 | 2/2001 | Bobroff |
| 6,726,641 B1 * | 4/2004 | Chiang et al. ............... 602/5 |
| 2002/0146536 A1 | 10/2002 | Bard |

FOREIGN PATENT DOCUMENTS

| | | |
|---|---|---|
| DE | 40 29 685 A1 | 3/1992 |
| DE | 198 12 756 A1 | 10/1999 |
| EP | 0 639 361 A1 | 2/1995 |
| GB | 1094893 | 12/1967 |
| GB | 2312643 A | 11/1997 |
| WO | WO 02/065940 A2 | 8/2002 |

* cited by examiner

COMPRESSION BRACE MATERIAL WITH SPACER FABRIC INNER LAYER

CROSS-REFERENCE TO RELATED APPLICATIONS

This is a continuation-in-part of prior U.S. patent application Ser. No. 10/004,469, filed Oct. 23, 2001 now U.S. Pat. No. 6,726,641, which is itself a continuation-in-part of U.S. patent application Ser. No. 09/846,332, filed May 2, 2001 now U.S. Pat. No. 6,508,776, priority from the filing date of which is hereby claimed under 35 U.S.C. § 120.

FIELD OF THE INVENTION

This invention generally relates to orthopedic supports and, more specifically, to a composite material for use in making elastic compression braces having improved compression support, body heat retention, and breathability during use.

BACKGROUND OF THE INVENTION

Elastic compression braces are available in many forms. Commonly, such braces are composed of soft, elastic material so that when worn, they provide a certain amount of support for an injured joint. These types of braces, often purchased without a prescription or the need for skilled professional fitting, have been used for a number of years and have been commonly available as braces for the knee, ankle, thigh, wrist, elbow, chest, or lower back. These resilient, pliable compression braces can be worn for sprains and strains, arthritis, tendonitis, bursitis, inflammation, to reduce discomfort during post-operative use, or to treat post-trauma discomfort.

The elastic compression braces are often made from synthetic rubber (e.g., polychloroprene). This particular material is desirable because of its combination of favorable properties useful in elastic compression braces. Polychloroprene rubber has good elasticity and a relatively high density, thereby providing good compression support and resistance to shear forces.

Polychloroprene rubber is a closed cell material and therefore does not dissipate heat very well during use. Its closed cell characteristics can be useful in retaining heat during use by reflecting emitted heat back into the bones and joints of the affected area. This localized concentration of heat can aid venous flow, help reduce edema, and make the soft tissues less susceptible to injury.

Although use of polychloroprene rubber in elastic compression braces can concentrate heat, the natural tendency of the closed cell material to prevent heat dissipation may cause problems for the user. When worn, the polychloroprene material braces are stretched to impart a compression load around the affected body area. This compression fit, combined with the high density of the material and the lack of air circulation and dissipation through the material, can result in heat discomfort and perspiration, and may lead to heat rashes. Prolonged use of such braces can cause the user to perspire constantly, resulting in discomfort to such a ° that the user often stops wearing the brace prematurely. In effect, the material itself dictates the length of time that the orthopedic brace can be worn. It is not uncommon for users to stop wearing such braces after about one to two hours. In an effort to provide better breathability, certain prior polychloroprene rubber braces have been manufactured with perforations or holes punched through the entire depth of the material. However, these braces may not retain sufficient structural integrity to serve as an effective compression brace for the wearer because neoprene material is removed from these braces.

Thus, there is a need for an elastic compression brace having sufficient structural strength and integrity to offer a sufficient level of compression support, while also dissipating heat during use to reduce or avoid undue perspiration and heat discomfort, especially during prolonged use.

SUMMARY OF THE INVENTION

The present invention provides a composite material for compression braces and the like, wherein the composite material includes an elastically stretchable first layer, a flexible second layer affixed to the first layer, a third layer comprising a spacer fabric affixed to the second layer, and a flexible fourth layer affixed to the third layer. The first layer may not be the outermost layer, as it is contemplated that an outer layer may cover the first layer.

In an embodiment of the invention, the elastic outer layer includes a plurality of slits therethrough to permit and promote transverse airflow through the composite material.

An embodiment of the present invention provides a flexible, resilient composite material for use in forming elastic compression braces for surrounding and supporting a body part by compression. The composite material includes a center elastic layer, an inner fabric layer, and an outer fabric layer. The elastic center layer is preferably composed of closed cell material in sheet form, having on one side thereof a plurality of grooves or channels formed therein to intersect each other to define a gridwork. The pattern of channels provides passageways along the width and length of the center layer to enable heat and moisture dissipation for the body part being supported.

The center layer also may have a plurality of cuts extending through the entire depth of the layer and distributed across the surface area of the layer, with the center layer still having sufficient structural strength and integrity to provide orthopedic compression support.

The composite material may also include an inner layer of flexible, resiliently elastic, porous fabric material bonded to the grooved side of the center layer. The outer fabric layer may also be composed of a flexible, resiliently elastic, porous material bonded to the non-grooved side of the center layer.

In an embodiment of the invention, the plurality of cuts extending through the center layer are arcuate slits—for example, circular slits extending between about 180° and 270°—the arcuate slits defining an array of tabs that are hingedly attached to the center layer, such that stretching the composite material produces gaps in the center layer, thereby creating an airflow path between the inner and outer layers.

In another embodiment of the invention, the composite material includes an elastic outer layer, a first fabric layer, a spacer fabric layer, and a second fabric layer. The spacer fabric layer provides a lightweight component that permits airflow laterally through the composite material.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
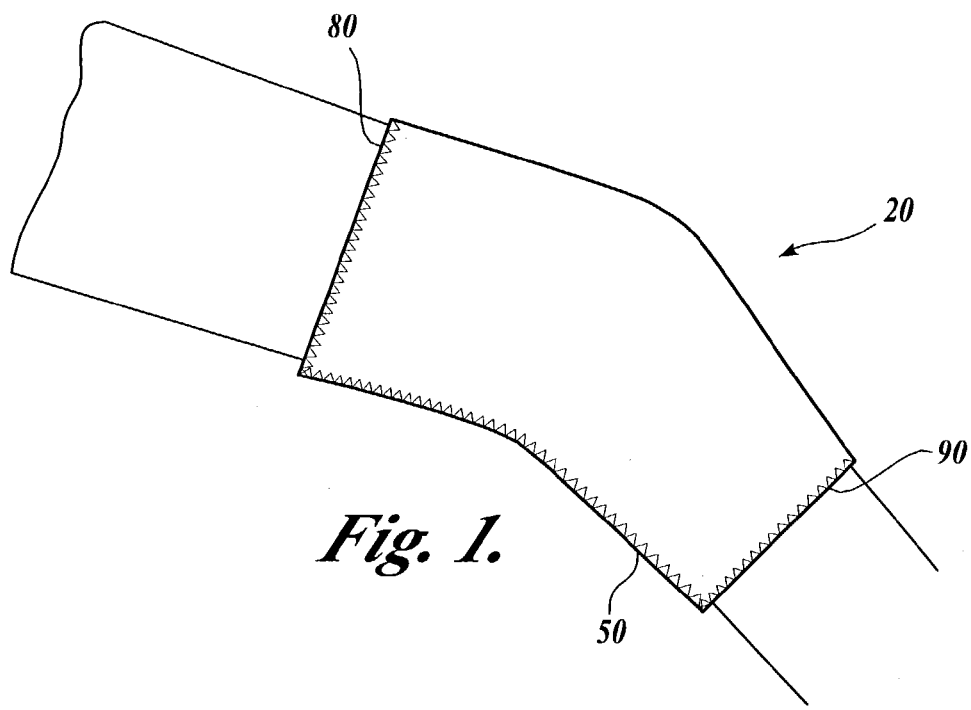
FIG. 1 is a side elevation view semi-schematically illustrating a knee brace made from an orthopedic material according to principles of the present invention.
Figure 2:
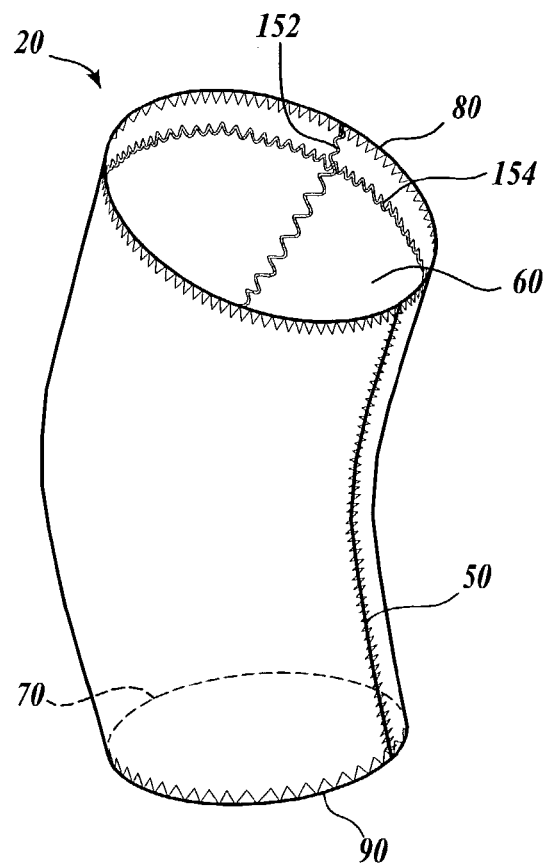
FIG. 2 is a semi-schematic perspective view of the knee brace shown in FIG. 1.
Figure 3:
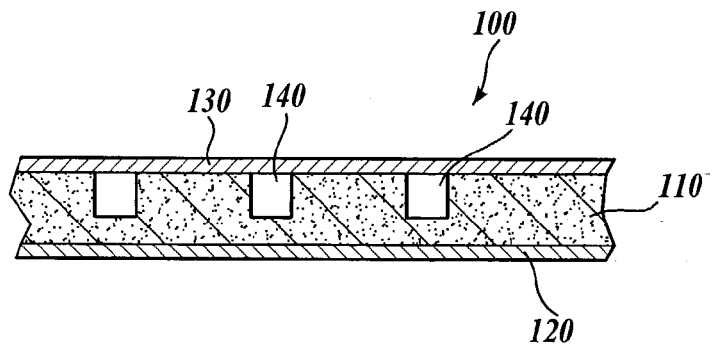
FIG. 3 is a cross-sectional view schematically illustrating components of a composite orthopedic material of the present invention.
Figure 4:
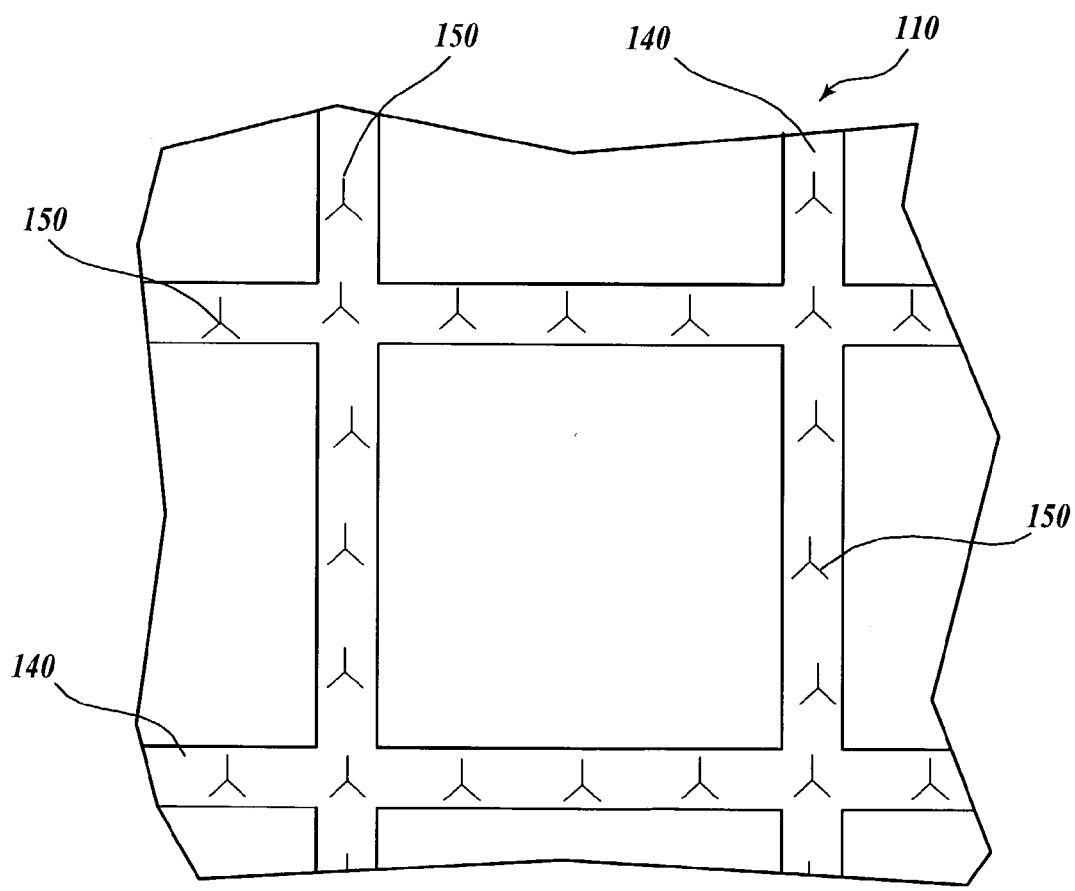
FIG. 4 is a frontal plan view illustrating a section of a punctured center layer of the composite material of the present invention.
Figure 5:
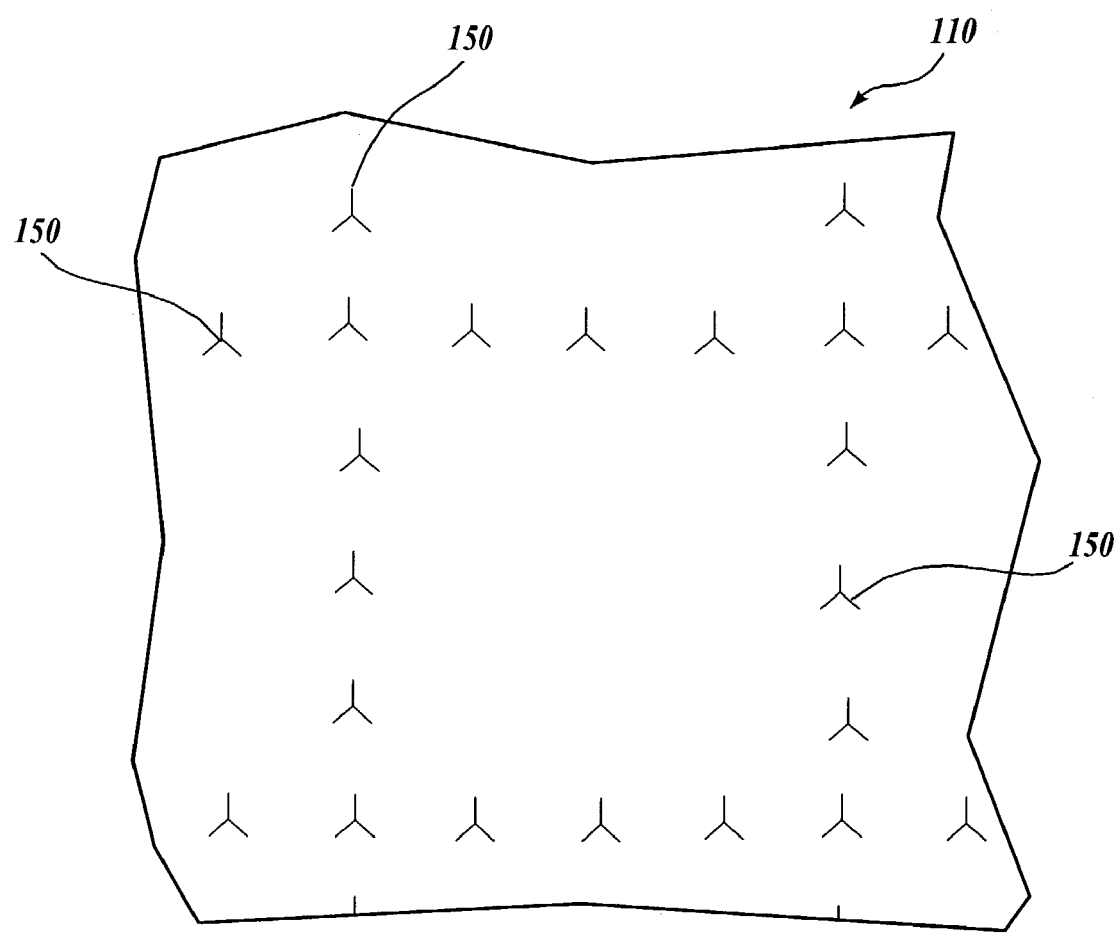
FIG. 5 is a back plan view illustrating a section of the punctured center layer shown in FIG. 4.

FIGS. 1 and 2 illustrate a knee brace 20 made from an orthopedic material according to principles of this invention. The orthopedic material is illustrated in FIGS. 3, 4, and 5. The knee brace is a soft orthopedic brace made from a flexible, resilient composite 100 shown in flat form in FIGS. 3, 4, and 5. The flat form composite material is cut to shape and sewn or otherwise assembled to form a tubular knee brace 20, illustrated in FIGS. 1 and 2.

Referring to FIGS. 1 and 2, a piece of composite material 100 in flat sheet form is folded over on itself. The overlapping long edges on the opposite side of the fold are fastened by a long, upright seam 50. The material in the flat is cut in a shape so that when stitched along seam 50, as shown in FIGS. 1 and 2, an angular knee support of generally tubular form is produced having an open top 60 and an open bottom 70. Peripheral stitching 80 at the upper edge and similar peripheral stitching 90 at the bottom edge provide finished edges for the completed knee support.

The components, which comprise the composite 100, are best understood by referring to FIGS. 3, 4, and 5. FIG. 3 shows a cross-sectional view illustrating the components of the composite 100 of the present invention. The composite material includes a flexible and foldable center elastic layer 110, an inner fabric layer 130, and an outer fabric layer 120. The center elastic layer 110 is preferably from a closed cell foam material in sheet configuration. One preferred elastic closed cell material is polychloroprene rubber, commonly known as neoprene rubber. Preferred neoprene materials are articles of commerce. Another suitable material for center layer 110 is styrene butadiene rubber (SBR). These materials are available in a wide density range, so it is not difficult to find material of a desired density that provides the desired level of support and provides good orthopedic compression during use. Ideally such material for the purposes of the present invention is from 1.5 mm to 8 mm thick. However, other thicknesses may be used. Also, other elastic closed cell materials may be used to form layer 110.

The center elastic layer 110 has formed therein on one side thereof a plurality of intersecting grooves or channels 140. In non-limiting example, one embodiment of the present invention shows the pattern of intersecting channels 140 is formed by placing neoprene sheet material down on a metal mesh and then placing a weighted heat source on top of the flat sheet material. The pressure and heat cause the mesh to depress into the sheet material to permanently take the shape of the metal mesh on the underside where the grid pattern of the metal mesh is pressing into the sheet material. In addition or alternatively, the mesh may be preheated.

In another embodiment of the present invention, a pattern of intersecting channels 140 is formed on both-surfaces of the sheet material. This can be accomplished in one manner by sandwiching the center layer 110 between top and bottom metal grids and heat pressing both grids against center layer 110, causing both grids to depress into the surfaces of the sheet material. The grid pattern may be identical on both sides of the center layer 110, or may be of different configurations.

In the embodiment shown in FIGS. 3 and 4, the plurality of intersecting channels 140 formed in center elastic layer 110 defines a generally rectangular or square-shaped pattern or grid. It is to be appreciated that the pattern can be of any other shape (e.g., diamonds (see FIG. 9), triangles, ovals, circles, etc.) as long as the channels 140 intersect each other so as to provide a continuous or interconnected passageway across the sheet material and along the length of the material.

The center elastic layer 110 may be punctured to form a multiplicity of punctures or cuts 150 through the layer. Cuts 150 are not shown in FIG. 3 for simplicity, but are shown in FIGS. 4 and 5. FIG. 4 is a frontal plan view showing a section of punctured center layer 110. FIG. 5 is a back plan view showing a section of the punctured center layer 110 shown in FIG. 4. The multiplicity of cuts 150 are dispersed across the surface of center elastic layer 110 and extends through the entire depth of the layer so that fluids, including perspiration and air, can pass through the cuts 150 from one side of the layer to the other, especially when the layer is stretched.

In one embodiment of the present invention, cuts 150 are located only in registry with the channel portions 140. In another embodiment, cuts 150 are located not only within the channels 140, but also in the ungrooved/channeled portion of elastic layer 110. In a further embodiment, the cuts 150' are located only at the intersections of the channels 140'. The multiplicity of cuts 150 may be of uniform pattern and spaced apart uniformly about the center elastic layer 110. Ideally, the multiplicity of cuts 150 should not be so large or the cuts must be spaced so close together that the overall structural integrity of the neoprene material is reduced beyond the ability of the material to provide sufficient orthopedic compression support during use.

The multiplicity of cuts 150 may define a cut pattern. FIGS. 4 and 5 show that the cut pattern has three "legs" that radiate from a common point. It is to be appreciated, however, that the cut pattern may be any shape, such as a straight line, a curved line, a cross, or a five-legged pattern, without departing from the scope of the present invention. It is to be further appreciated that preferably the puncture does not actually remove any significant material, if any, from center elastic layer 110 or channels 140; rather, the puncture simply extends through the channels. Thus, the puncture does not form a hole or passage through the neoprene material unless the material is stretched.

The pattern for the multiplicity of cuts 150 may be formed in center elastic layer 110 by a number of methods. One such method of forming a cut pattern in the neoprene material is by a roller having a cylindrical outer surface with projecting punches in the desired cut pattern so that rolling the roller over the flat surface of the neoprene material punches out cuts in the desired pattern.

Referring back to FIG. 3, composite material 100 also includes a soft, flexible, resilient, porous inner fabric layer 130. Inner layer 130 may be a knitted flexible and foldable, stretchable cloth fabric material, which is porous to air and water because of the pores inherently formed by the knitted fabric. Composite material 100 also includes a flexible and elastic, porous outer fabric layer 120, which also may be made from a stretchable knitted fabric of the same or different type from layer 130. The inner and outer fabric layers 130 and 120, respectively, may also be made from other stretchable knitted fabrics including nylon, Dacron™ or other synthetic fibers.

After the center elastic layer 110 is altered with a plurality of intersecting channels 140 on one side thereof and punctured with a cut pattern 150, inner fabric layer 130 is bonded to the grooved face of center layer 110, while outer fabric layer 120 is bonded to the non-grooved face of center layer 110. Inner fabric layer 130 may be adhered to the center layer 110 using an adhesive technique that prevents the glue or other adhesive from being placed in channels 140. As such, the adhesive does not close or obstruct channels 140. Outer fabric layer 120 is also glued or otherwise adhered or bonded to center layer 110. The adhesive bonds the entire contacting surface areas of the center layer 110 and the adjoining inner and outer fabric layers 130 and 120, respectively. It is to be noted that the adhesive does not disrupt the porosity of the center layer 110 and the inner or outer layers 130 and 120.

Returning to FIGS. 1 and 2, knee brace 20 is intended to be worn with the grooved/channeled side facing the body of the wearer. This provides the advantageous result of retaining heat against the body while allowing knee brace 20 to be breathable. Furthermore, because knee brace 20 is made from the composite material, it has sufficient porosity that internal heat build-up during use is essentially avoided. Knee brace 20 also provides good compression around a body part supported by knee brace 20 in its stretched condition. The elastic center layer retains substantially all of its ability to apply a compression load on the body portion being braced because material is not actually removed from the neoprene center layer, as in some conventional braces. Additionally, knee brace 20 is of sufficient density due to the neoprene, SBR, or other selected material to provide the compression necessary to serve as a useful knee brace. The inner and outer layers 130 and 120 also provide additional compressive strength to knee brace 20.

Knee brace 20 also provides good breathability. When knee brace 20 is in use, it stretches in a bidirectional manner, thereby creating a pumping action to allow air to flow through the channels 140 of knee brace 20. This carries body sweat through channels 140 and out the ends of knee brace 20. Knee brace 20 also allows fresh, cool air to pass inwardly through knee brace 20 to reach the body. Correspondingly, a certain amount of heat is able to pass from inside knee brace 20 to the outside through the plurality of cuts 150, which opens up as the brace is stretched during use.

In accordance with a further aspect of the present invention, silicone 152, in the form of a gel or beads, may be applied along the inside of knee brace 20 lengthwise of the brace, perhaps on opposite sides of the brace. Additionally or alternatively, the silicone beads 154 may be placed circumferentially around the inside of the brace, perhaps near the ends of the brace. The silicone may be applied in a stripe of some width, in a narrow line or band, or in other patterns. Moreover, the stripe or line of silicone may be straight or curved. This silicone material causes the brace to stay in place on the body due to the friction between the silicone and the body. The silicone does not, however, cause discomfort or undue rubbing against the body.

In one embodiment, the silicone may be applied to the interior of knee brace 20 after the brace has been fully constructed. In another embodiment, the silicone is applied to the inside of inner fabric layer 130 of knee brace 20 and then the inner layer 130 is applied to the inside surface of center layer 110. As those skilled in the art will appreciate, other materials, in addition to silicone, may be employed to cause the brace to stay in place on the body without departing from the scope of the present invention.

Figure 6:
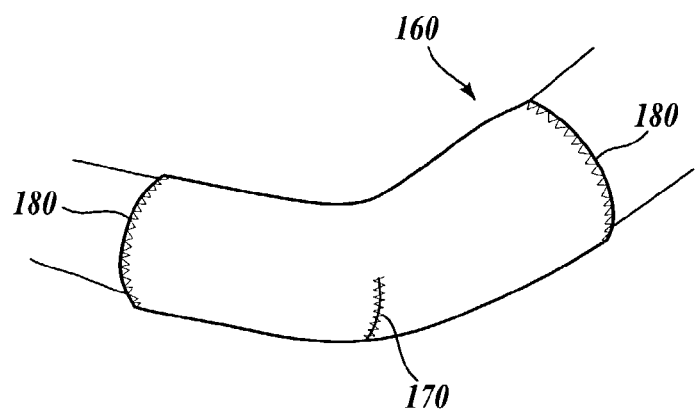
FIG. 6 is a perspective view illustrating an elbow brace made from the composite material of the present invention.
Figure 7:
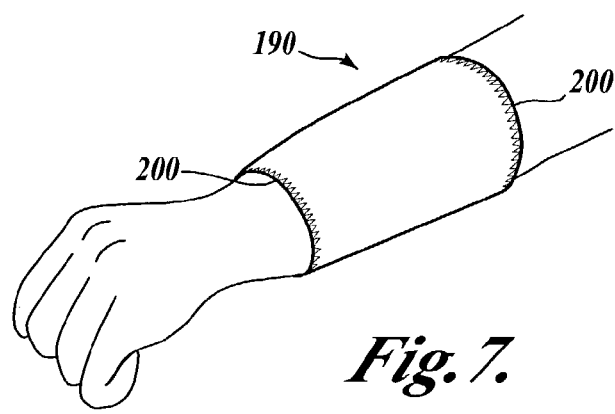
FIG. 7 is a perspective view illustrating a wrist brace made from the composite material of the present invention.
Figure 8:
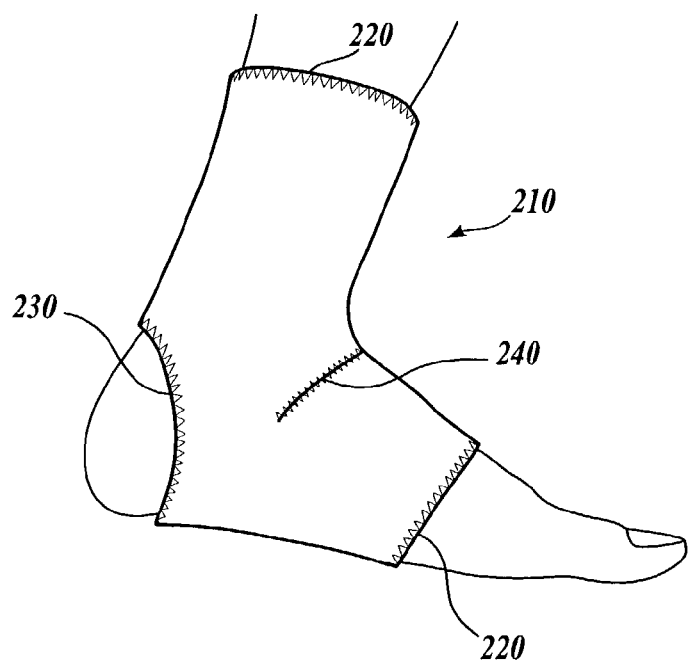
FIG. 8 is a side view illustrating an ankle brace made from the composite material of the present invention.

FIGS. 6–8 illustrate further uses of the composite material 100 in compression braces. FIG. 6 shows an elbow brace 160 in which composite material 100 is folded and seamed along its length. The brace may have an intermediate seam 170 to form a generally L-shaped tubular elastomeric brace. The top and bottom edges of the tubular brace have stitched peripheral seams 180 for edge reinforcement. FIG. 7 illustrates a wrist brace 190 made from the composite material 100, in which the material is folded and seamed lengthwise to form a generally straight tubular brace having peripheral stitching 200 at its opposite ends for edge reinforcement. FIG. 8 illustrates an ankle brace 210 made from composite material 100. The ankle brace 205 is formed as a generally L-shaped tubular brace with peripheral stitching 220 at its opposite ends, peripheral stitching 230 around an edge portion of the brace that fits around the heel of the user. The brace may include intermediate stitching 240 fastening adjoining intermediate edges of the L-shaped ankle support.

These compression braces can be used to provide required levels of anatomical compression support while improving ventilation to the supported area to reduce the discomfort caused by perspiration and overheating. The improved composite material of this invention thus improves the anatomical support provided by compression braces formed when such materials build up, because the user is able to wear the brace for extended periods, rather than having removed the brace prematurely because of heat discomfort.

Figure 9:
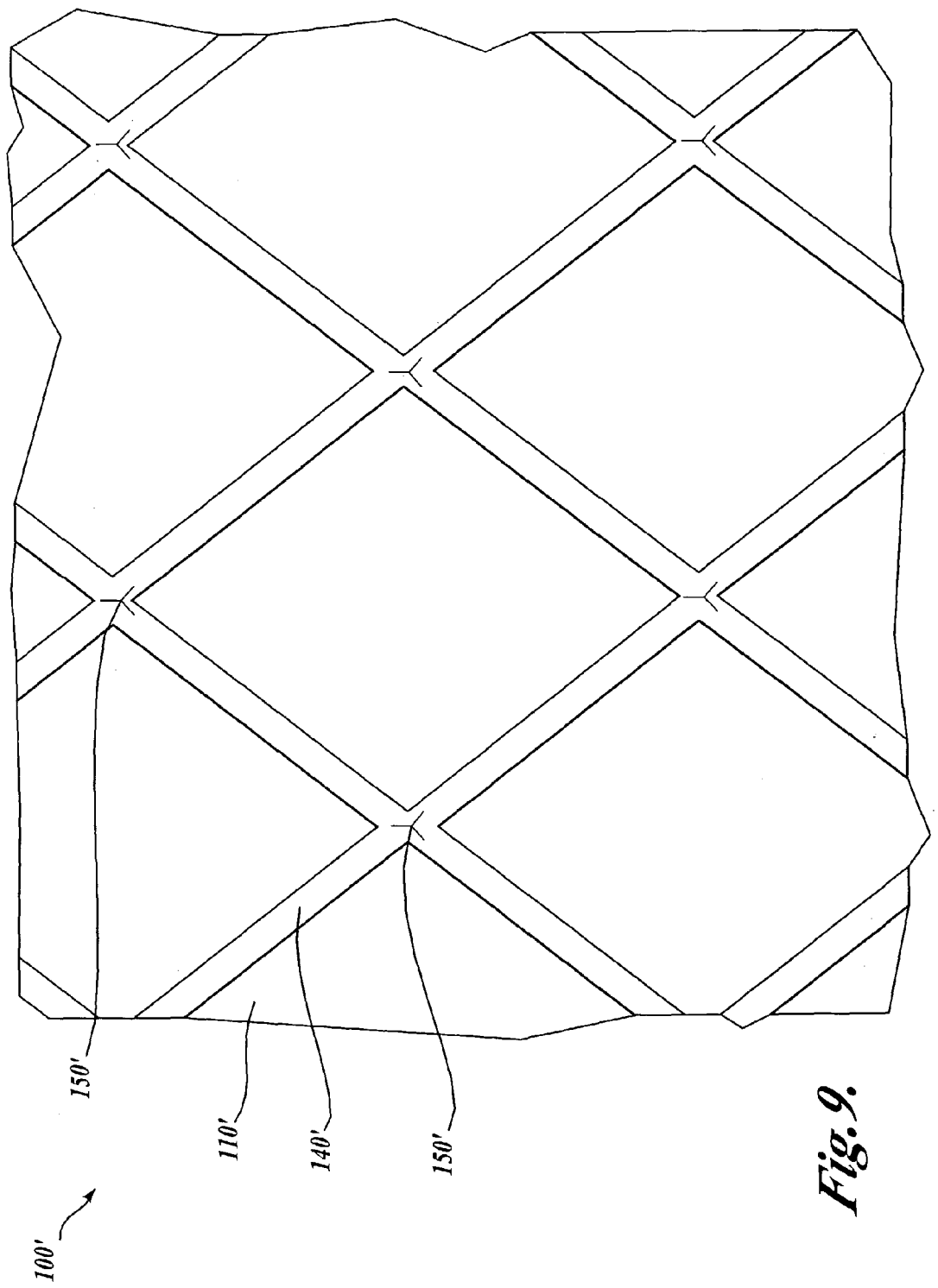
FIG. 9 is a view similar to FIG. 4, illustrating another pattern of channels formed in the center layer of the composite material.

FIG. 9 illustrates an alternative embodiment to the present invention wherein the composite material 100' is formed with an elastic center layer 110' having intersecting channels formed therein in a diamond pattern. Also, the cuts 150' are located at the intersection of the channels 140'. The channels 140' and cuts 150' may be formed in a same or similar manner as described above with respect to center layer 110. Further, in other respects, the composite material 100' may be the same or similar to material 100 described above.

Figure 10:
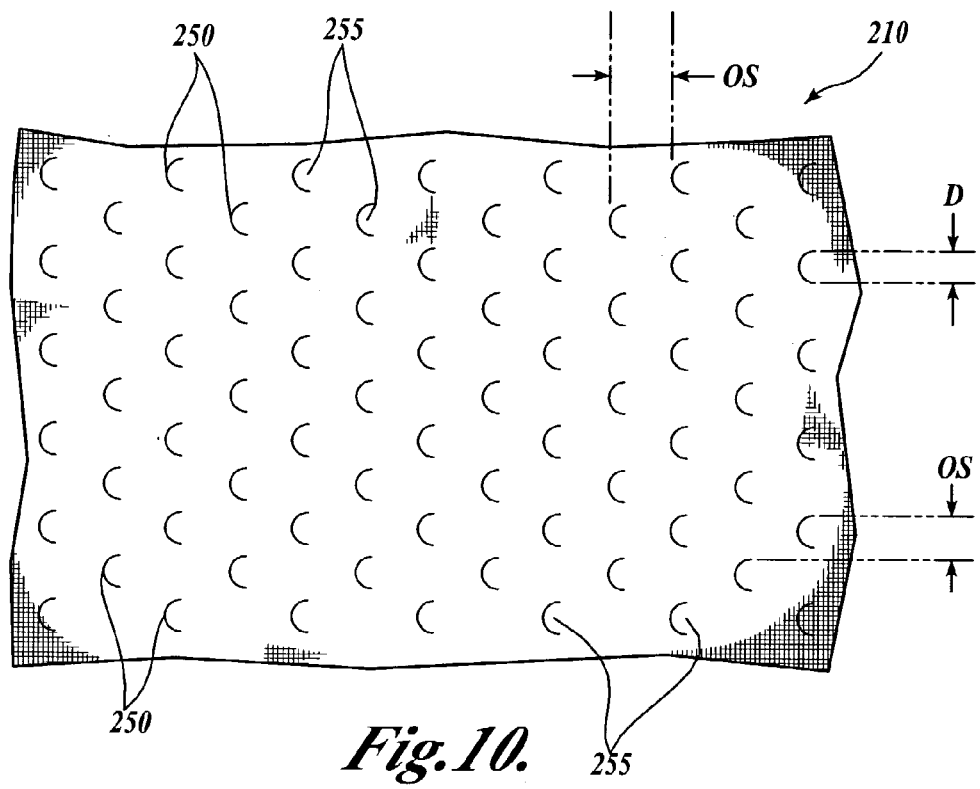
FIG. 10 is a plan view of a center layer according to another embodiment of the present invention.

FIG. 10 illustrates a center layer 210 for a third embodiment of a composite material in accordance with the present invention. In this embodiment, the center layer 210 is provided with a plurality of arcuate slits 250 that extends entirely through the thickness of the center layer 210. The arcuate slits 250 are preferably semi-circular or partially circular slits defining approximately 180° to 270° of a full circle. The arcuate slits 250 define a plurality of tab portions 255 that remain hingedly attached to the center layer 210, but that can open to allow airflow through the center layer 210. The curved geometry of the slits 250 provides a relatively long slit in a relatively short transverse distance on the center layer 210.

The plurality of arcuate slits 250 is arranged in a rectangular, offset array, as shown in FIG. 10. The center layer 210 is preferably between about 1.5 mm and about 8 mm thick and, most preferably, about 3 mm thick. The arcuate slits 250 have a diameter D that is preferably between about 3 mm and about 10 mm, and most preferably approximately 4 mm. Adjacent offset lines of slits are spaced apart (in both the vertical and the horizontal direction as shown in FIG. 10) by an offset denoted OS, which is preferably between about 3 mm and about 10 mm, and most preferably, about 6 mm. A composite material utilizing the center layer 210 in combination with inner and outer layers 120, 130 (not shown in FIG. 10) discussed above, has been found to produce adequate compressive strength for use in orthopedic applications, such as compression braces.

The slits 250 are produced in the center layer 210 without removing a significant amount of material from the center layer 210, whereby when the center layer is relaxed, or unstretched, the slits 250 are substantially closed.

Figure 11:
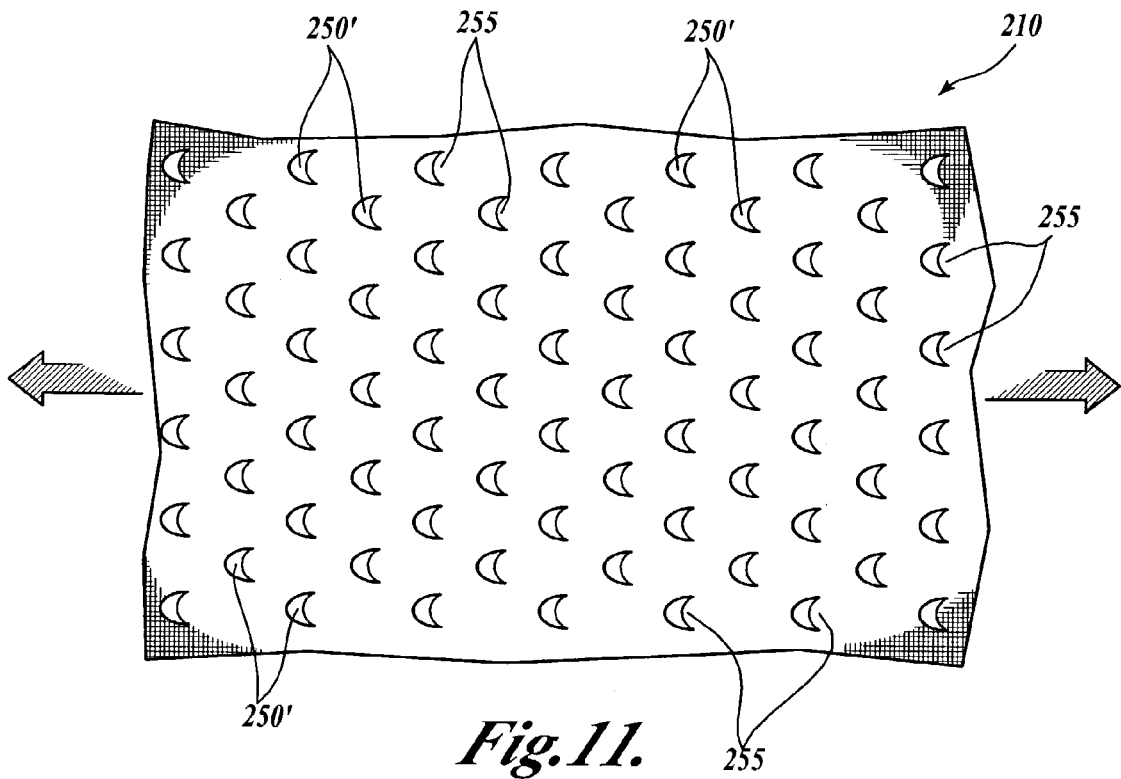
FIG. 11 is a plan view of the center layer shown in FIG. 10 with the center layer stretched lengthwise, as indicated with the large arrows.

FIG. 11 shows the center layer 210 of FIG. 10, with the composite material stretched elastically in the lengthwise direction (i.e., left and right in FIG. 11). Crescent-shaped airflow channels 250' are opened in the stretched panel 210. It will be appreciated that the curvature of the arcuate slits 250 produces a relatively large flow area for air and moisture to pass across the center layer 210. This is due in part to the geometry of the tab portions 255, which are hingedly connected to the center layer 210 along one edge, which partially isolates the tab portions 255 from the stretching stresses in the center layer 210. The tab portions 255 therefore do not stretch as much as the surround portion of the material opposite the tab portions 255, producing a larger airflow channel 250'.

When the center layer 210 is relaxed, i.e., when the stretching forces are removed, the crescent-shaped airflow channels 250' close, substantially returning to the slits 250 shown in FIG. 10. In particular, the tab portions 255 move laterally relative to the surrounding material opposite the tab portions 255. This opening and closing motion of the tab portions 255 produces a pumping action within the airflow channel 250' enhancing the flow of air through the center layer 210. It will be appreciated that when a soft compressive brace is worn, such as the knee brace shown in FIGS. 1 and 2, movement of the wearer will result in elastic flexure of the brace. Such flexure of a brace made from the composite material described above will therefore produce an air pumping action, improving airflow across the brace. Moreover, when the wearer is relatively still, less heat is generated by the wearer and less airflow will be produced by the pumping action through the air channels 255'.

Figure 12:
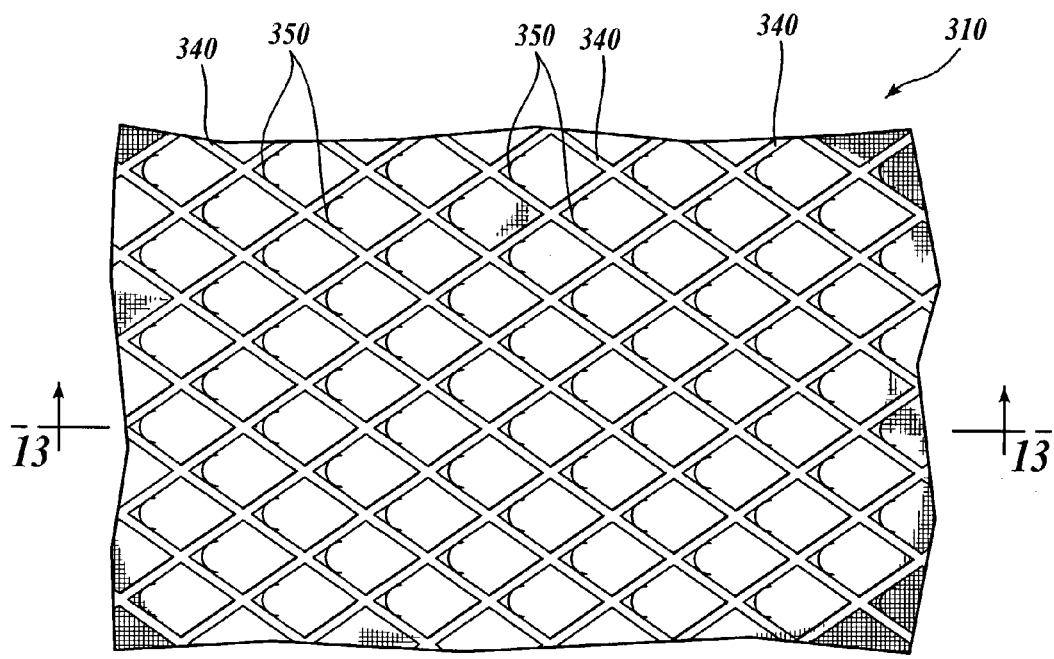
FIG. 12 is a plan view of a center layer according to another embodiment of the present invention.
Figure 13:
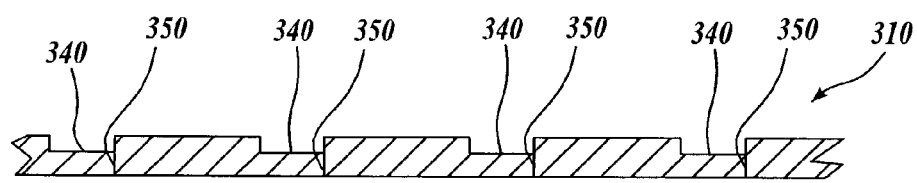
FIG. 13 is a cross-sectional view of the center layer shown in FIG. 12, taken along line 13—13.

A center layer 310 for a fourth embodiment of the present invention is shown in FIG. 12, wherein a center layer 310 substantially identical to the center layer 210 (shown in FIG. 11) is provided with a plurality of elongate, shallow grooves or channels 340 that extends laterally across the inner face of the center layer 310. As discussed in detail above, the network of intersecting grooves 340 provides channels that promote airflow adjacent the wearer's skin, along the inner face of the composite material. As seen most clearly in FIG. 13, which shows a cross-sectional view of the center layer, the slits 350 are preferably positioned directly adjacent or intersecting the grooves 340, so that air and vapor are directed towards the slits 350; or conversely, air entering from the slits is directed toward the grooves 340.

Figure 14:
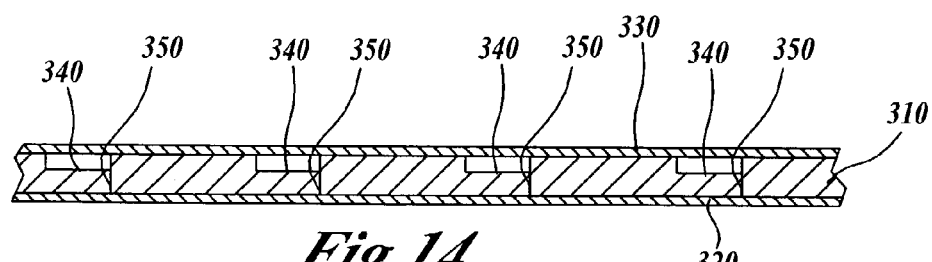
FIG. 14 is a cross-sectional view of the center layer shown in FIG. 13, shown with inner and outer layers attached to the center layer.
Figure 15:
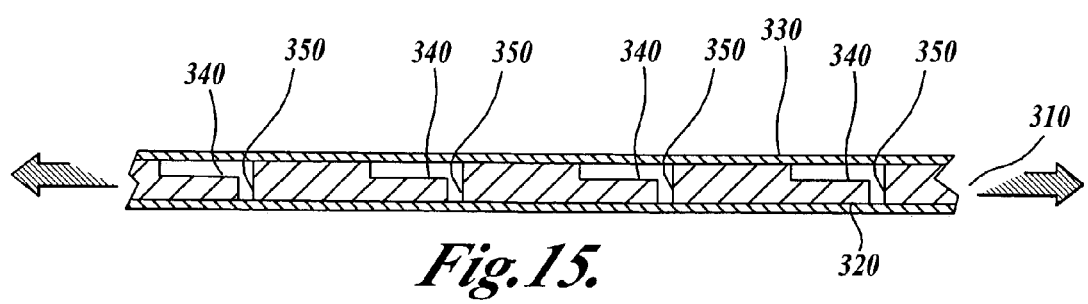
FIG. 15 is a cross-sectional view similar to FIG. 14, showing the composite material stretched lengthwise, as indicated with the large arrows.

FIGS. 14 and 15 show a cross section of a composite material 300 utilizing the center layer 310. The composite material 300 includes an elastic inner fabric layer 330, preferably a knitted synthetic fiber layer, that is adhered to the inner surface of the center layer 310. An elastic outer fabric layer 320 is adhered to the outer surface of the center layer 310. The inner and outer layers 320, 330 are adhered to the center layer in a manner that will permit at least some of the arcuate slits 350 to open when the composite material is stretched.

The inner and outer layers 320, 330 are porous such that air and vapor can pass through the inner layer 330, through the arcuate slits 350 (when the slits are open) and through the outer layer 320 to vent gasses away from the wearer, and in the opposite direction to provide cooling air beneath the composite material. FIG. 15 shows the composite material 300 stretched laterally, i.e., left to right in FIG. 15. The slits 350 are in an open position due to the stretching of the fabric. FIG. 14 shows the composite material 300 in an unstretched configuration, wherein the slits 350 are substantially closed. It will be appreciated by comparing FIG. 15 with FIG. 14 that sequential flexing and unflexing (stretching and unstretching) of the composite material will produce the pumping action discussed above, to facilitate the passage of air through the composite material.

Although the slits of the preferred embodiment are semi-circular (i.e., 180°–270° of a circular arc), any number of other shapes are possible and contemplated herein. For example, slits producing elongate tab portions with curved free ends and hingedly attached back ends may be utilized.

Figure 16:
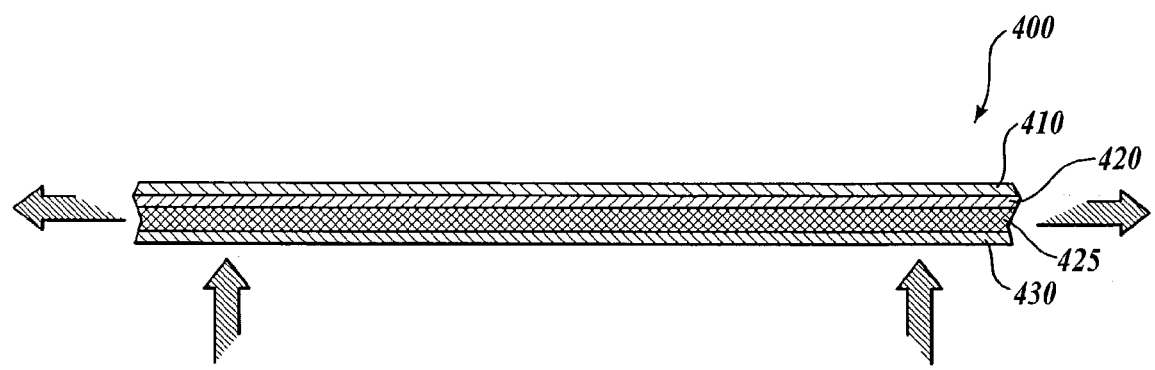
FIG. 16 is a fragmentary cross-sectional view of another embodiment of the present invention using a spacer fabric.

Another embodiment of a compression brace material 400 according to the present invention is shown in FIG. 16. In this embodiment, the multiple-layer compression brace material 400 is a sandwiched construction including: (i) a flexible outer layer 410, preferably made of a closed cell foam material such as neoprene; (ii) a first fabric layer 420 attached to the outer layer 410; (iii) a spacer fabric layer 425 attached to the first fabric layer; and (iv) a second fabric layer 430 attached to the spacer fabric layer 425. In one embodiment, the layers are attached to each other with an adhesive, although other attachment mechanisms may be used as are well known in the art, including stitching.

Figure 17:
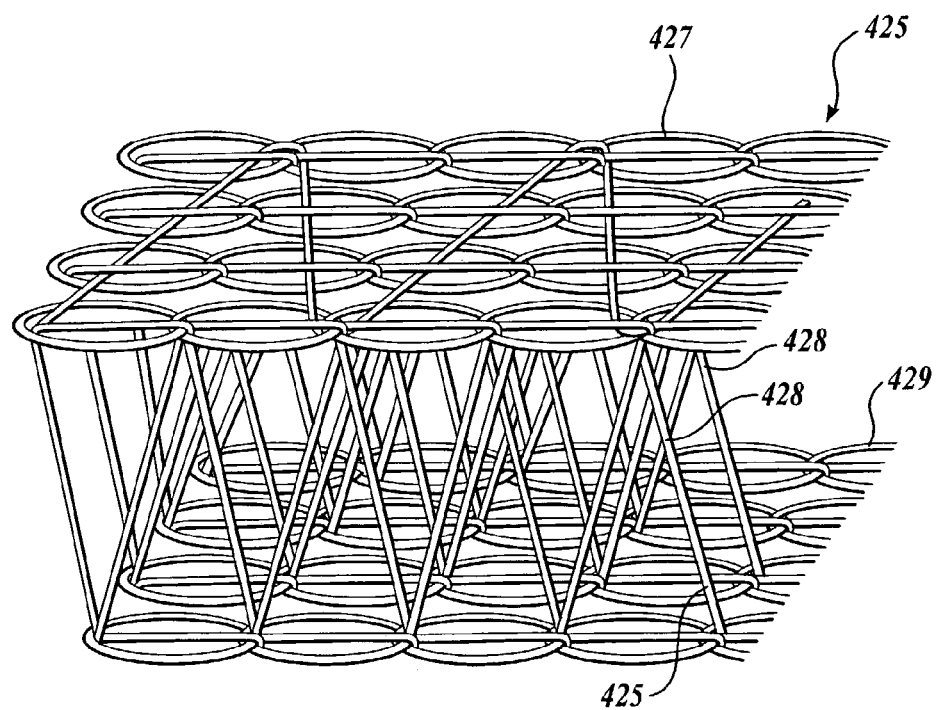
FIG. 17 is a fragmentary perspective view of the spacer fabric of FIG. 16, shown in isolation.

Spacer fabrics, as used herein, refers to 3D textiles typically fabricated on warp knitting machines such as rib-knitting Raschel machines. FIG. 17 shows a somewhat stylized cross-sectional view of the spacer fabric 425 in isolation. The spacer fabric 425 is characterized by a pair of spaced-apart faces 427, 429, sometimes called ground fabrics, that are interconnected by a plurality of transverse strands or spacer threads 428, to produce a porous, lightweight fabric. The spacer threads 428 are spaced relatively far apart, relative to the strand thickness, producing a three-dimensional porous mesh that has the advantage in the present invention of permitting airflow between and at least in part parallel to the faces 427, 429. A suitable spacer thread 428 is usually a polyamide or polyester monofilament. Suitable spacer fabrics may range in thickness from less than 1 mm thick to 10 mm or more.

Referring again to FIG. 16, and as indicated by the arrows therein, the brace material 400 of the present invention permits air, heat, and evaporated sweat to pass transversely through the second fabric layer 430, and then generally laterally along the spacer fabric 425 toward the edges of the brace material 400. It has been found that this composite structure provides a particularly comfortable compression wrap. The superior performance is believed to be associated with the fact that, in use, the compression material 400 is elastically wrapped about a portion of the user. The user's motion while wearing the material causes elastic deformations in the brace material 400 and, in particular, in the spacer fabric 425. The spacer fabric 425 alternately compresses and relaxes somewhat during use, producing a pumping action to facilitate airflow through and along the spacer fabric 425. Therefore, the material permits and promotes some airflow near the user's body, while the elastic outer layer 410 helps to retain heat overall near the user, and to promote heat therapy over the wrapped body portion. The outer layer 410, in cooperation with the other fabric layers 420, 425, and 430 also provides the desired compression to the user. It will also be appreciated that, although the elastic outer layer 410 is shown in the disclosed embodiment as the outermost layer, it is contemplated by the present invention that another layer, such as a flexible facing, may be attached to the outer face of the outer layer 410, for example, to improve the aesthetic appearance of the material, to protect the outer layer from debris, to make the outer surface more slick, and for other reasons as are known in the art.

Figure 18:
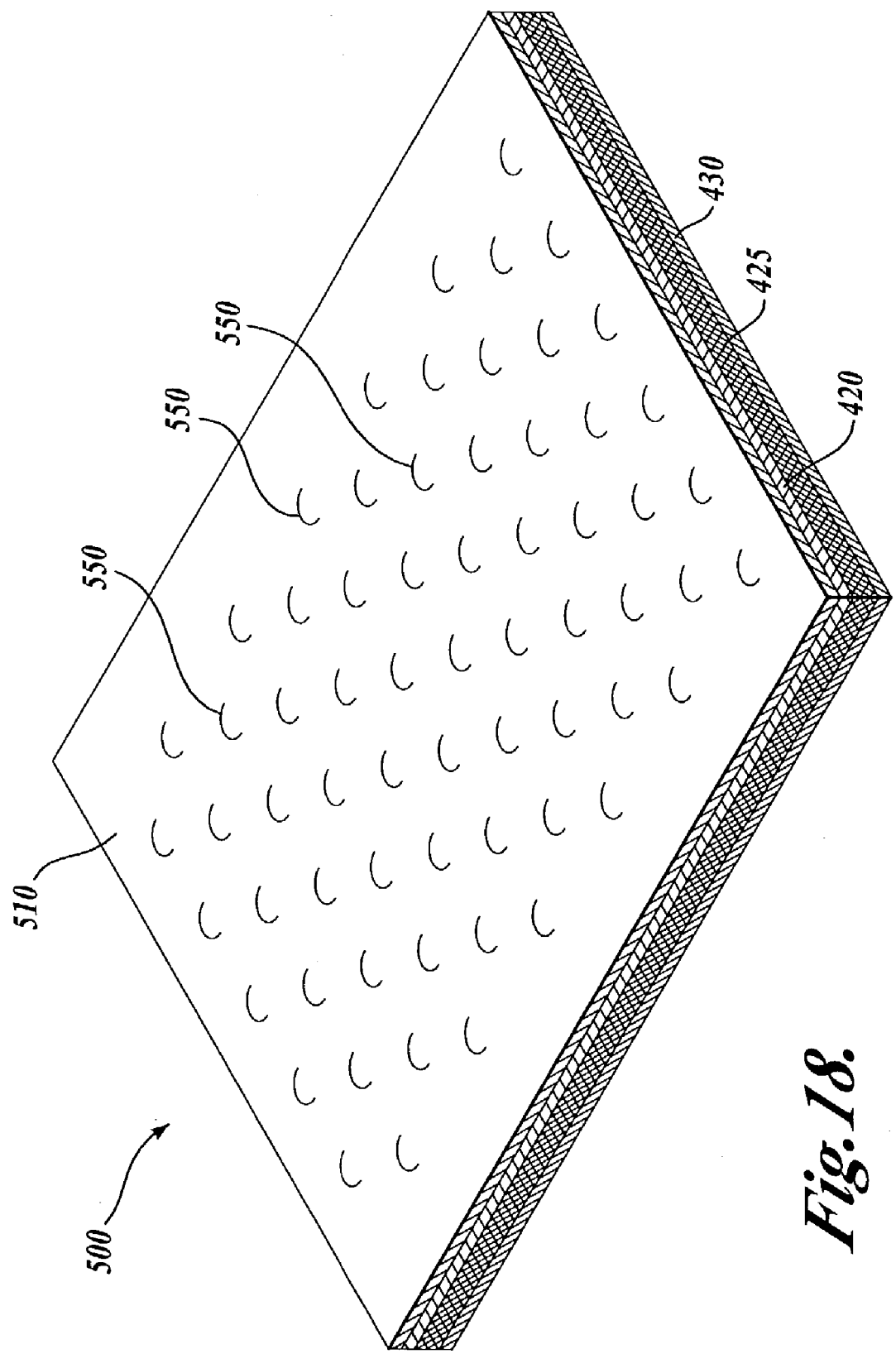
FIG. 18 is a perspective view of an embodiment of the present invention using a spacer fabric and an outer layer having slits therethrough.

FIG. 18 shows another embodiment of the compressive brace material 500, that is substantially similar to the compressive brace material 400 described above, including an outer layer 510, first and second fabric layers 420, 430, and a spacer fabric layer 425 therebetween. In this embodiment, however, the outer layer 510 includes a plurality of slits 550 through the thickness of the outer layer 510, permitting enhanced ventilation through the compressive brace material 500. The advantages of the plurality of slits through the outer layer 510 are discussed in some detail above with regard to the embodiments shown in FIGS. 5 and 10. Although arcuate slits 550 are shown in FIG. 18, it will be apparent that other slit shapes could alternatively be used, including single straight slits, angled slits, and the like.

It will also be readily appreciated that the outer layer 510 may include a plurality of transverse grooves or channels 340 (shown in FIG. 12) along its inner face, thereby providing another transverse channel for airflow along and through the compressive brace material 500. The aspects and advantages of the transverse channels 340 are discussed in detail above.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A composite material for use in constructing compression braces, the composite material comprising:
 a first layer comprising an elastically stretchable material having an inner face and an outer face;
 a flexible second layer having an outer face affixed to the first layer inner face, the second layer further having an inner face;
 a third layer comprising a spacer fabric having an outer face affixed to the second layer inner face, the third layer further having an inner face; and
 a flexible fourth layer having an outer face affixed to the third layer inner face.

2. The composite material of claim 1, wherein the first layer comprises a closed cell material.

3. The composite material of claim 1, wherein the first layer further comprises a plurality of slits therethrough.

4. The composite material of claim 3, wherein the plurality of slits in the first layer are arcuate.

5. The composite material of claim 3, wherein the second and fourth layers comprise knitted sheets of fabric made from synthetic fibers.

6. The composite material of claim 5, wherein a plurality of longitudinal channels are formed in the inner face of the first layer.

7. The composite material of claim 1, wherein the layers are affixed with an adhesive.

8. The composite material of claim 1, wherein the spacer fabric comprises a pair of spaced-apart ground fabrics interconnected by a plurality of transverse strands.

9. The composite material of claim 8, wherein the spacer fabric is produced on a rib-knitting Raschel machine.

10. The composite material of claim 8, wherein the spacer fabric has a thickness in the range of 1 mm to 10 mm.

11. A compression brace comprising an elastic tubular structure formed from a sheet of the composite material of claim 1, wherein the tubular structure is formed by sewing oppositely disposed edges of the composite material sheet together.

12. The compression brace of claim 11, wherein the compression brace is a unitary member comprising first and second tubular portions that are angularly connected.

13. A composite orthopedic support material comprising:
 a first panel made from an elastically stretchable material, the first panel having an inner face and an outer face;
 a porous, elastic second panel attached to the first panel and overlying the inner face of the first panel, the second panel having an inner face;
 a third panel comprising a spacer fabric, the third panel attached to the second panel and overlying the inner face of the second panel, the third panel further having an inner face; and
 a porous, elastic fourth panel attached to the third panel and overlying the inner face of the third panel.

14. The composite orthopedic support material of claim 13, wherein the first panel comprises a polychloroprene elastomer.

15. The composite orthopedic support material of claim 14, wherein the porous, elastic second and fourth panels comprise a knitted sheet of material made from synthetic fibers.

16. The composite orthopedic support material of claim 13, wherein the first panel inner face includes a plurality of arcuate slits therethrough.

17. A compression brace comprising an elastic tubular structure formed from a sheet of the composite material of claim 13, wherein the tubular structure is formed by sewing oppositely disposed edges of the composite material sheet together.

18. The compression brace of claim 17, wherein the compression brace is a unitary member comprising first and second tubular portions that are angularly connected.

* * * * *